United States Patent [19]

Kinney et al.

[11] Patent Number: 5,245,648
[45] Date of Patent: Sep. 14, 1993

[54] X-RAY TOMOGRAPHIC IMAGE MAGNIFICATION PROCESS, SYSTEM AND APPARATUS THEREFOR

[75] Inventors: John H. Kinney, Danville, Calif.; Ulrich K. Bonse, Dortmund, Fed. Rep. of Germany; Quintin C. Johnson, Livermore, Calif.; Monte C. Nichols, Livermore, Calif.; Ralph A. Saroyan, Livermore, Calif.; Warren N. Massey, Livermore, Calif.; Rudolph Nusshardt, Waltrop, Fed. Rep. of Germany

[73] Assignee: The United States of America as represented by the United States Department of Energy, Washington, D.C.

[21] Appl. No.: 681,269

[22] Filed: Apr. 5, 1991

[51] Int. Cl.⁵ .............................................. G21K 7/00
[52] U.S. Cl. ........................................ 378/43; 378/4; 378/145; 378/85
[58] Field of Search .................. 378/43, 85, 145, 4

[56] References Cited

U.S. PATENT DOCUMENTS 5,016,267  5/1991  Wilkins .................... 378/85

FOREIGN PATENT DOCUMENTS 2-16500  2/1990  Japan .................... 378/43

*Primary Examiner*—Craig E. Church
*Attorney, Agent, or Firm*—Henry P. Sartorio; Roger S. Gaither; William R. Moser

[57] ABSTRACT

A computerized three-dimensional x-ray tomographic microscopy system is disclosed, comprising:
a) source means for providing a source of parallel x-ray beams,
b) staging means for staging and sequentially rotating a sample to be positioned in the path of the
c) x-ray image magnifier means positioned in the path of the beams downstream from the sample,
d) detecting means for detecting the beams after being passed through and magnified by the image magnifier means, and
e) computing means for analyzing values received from the detecting means, and converting the values into three-dimensional representations. Also disclosed is a process for magnifying an x-ray image, and apparatus therefor.

21 Claims, 17 Drawing Sheets

X-RAY TOMOGRAPHIC IMAGE MAGNIFICATION PROCESS, SYSTEM AND APPARATUS THEREFOR

The United States Government has rights in this invention pursuant to Contract No. W-7405-ENG-48 between the U.S. Department of Energy and the University of California for the operation of Lawrence Livermore National Laboratory.

FIELD OF THE INVENTION

The present invention relates to an x-ray tomographic image magnification process, to microscopy systems and to apparatus for use therein. More particularly, it relates to an x-ray tomographic microscopy system containing an image magnifier which enables three-dimensional images of high resolution to be achieved.

BACKGROUND OF THE INVENTION

Computerized axial tomography systems or machines, i.e., CAT scanners, have been used for a number of years to obtain three-dimensional images from two-dimensional data. These systems have been used primarily by the medical profession to obtain three-dimensional pictures of the body, but they also have been used in industry for a variety of purposes.

Typically, the system comprises a source of x-rays, a sample positioned in the path of the x-rays, a detection system and an analyzing computer.

Conventional computerized tomography (CT) measurements for industrial purposes involve collecting absorption information for a single cross-sectional slice through a material. Spatial resolution is achieved by either collimating an incident beam using a pinhole and then rastering the beam across the sample, or by using a position sensitive-linear photodiode array to measure all the projection data for a single angular view in parallel.

There are disadvantages to both of these systems. The primary disadvantage of using the pinhole is that most of the incident radiation is thrown away. As a consequence, the rastering technique is extremely time consuming. Acquiring the data for reconstruction of a single sample takes upwards to twelve hours.

The photodiode array is noisy and subject to non-linearities. The noise limits the dynamic range, and therefore, the maximum contrast that can be studied in a sample. The non-linearities also introduce ring-like artifacts in the reconstructions which can further reduce the usefulness of the information obtained. Finally, it still requires days to obtain enough information for three-dimensional sample visualization.

THE PRIOR ART

A high resolution tomography system with chemical specificity is described by Bonse et al., in an article in Nucl. Instrum. Methods A246,644 (1986). This system utilizes parallel beam synchrotron x-rays from an electron storage ring. The beams are passed sequentially through a double crystal monochromator, a collimator, the sample to be analyzed, a second monochromator, a scintillator which converts the x-rays to visible light, and a lens which Projects the light onto a charge coupled device. The charge coupled device records the intensity of the light and this value is stored in a computer. The sample is then rotated by a small angle and another two-dimensional absorption image is obtained. The process continues until 180° of sample rotation has been recorded and the information stored in a computer. Tomographic software converts x-ray absorption profile data into two-dimensional reconstructions of the linear attenuation coefficients in the sample interior. These values are rendered into a three-dimensional view by means of high-speed, digital, image processing computers.

The system described is a vast improvement over previous techniques, achieving spatial resolution of the order of 2-5 $\mu$m.

This order of resolution is sufficient for many purposes. However, even finer resolution is needed when the object is to discriminate between micrometer size objects and flaws in such materials as mineralized tissues or man-made composite microstructures.

Higher resolution can be achieved by magnifying the x-ray images after the x-rays have passed through a sample.

It is, therefore, an object of this invention to provide a process for magnifying x-ray images in a computerized axial tomography system.

It is a further object of this invention to provide a computerized x-ray tomographic microscopy process having improved signal to noise ratios and improved spatial resolutions of x-ray images.

It is a still further object of this invention to provide an improved computerized x-ray tomographic microscopy system having improved signal to noise ratios and spatial resolution as compared to the systems of the prior art.

It is yet another object of this invention to provide an improved computerized x-ray tomographic microscopy system containing an image magnifier which enables three-dimensional images of high resolution to be achieved.

It is a still another object of this invention to provide an x-ray image magnifier for use in a computerized tomography system.

· Other objects and advantages of the invention will be apparent from the description, drawings and claims to follow.

SUMMARY OF THE INVENTION

Figure 1:
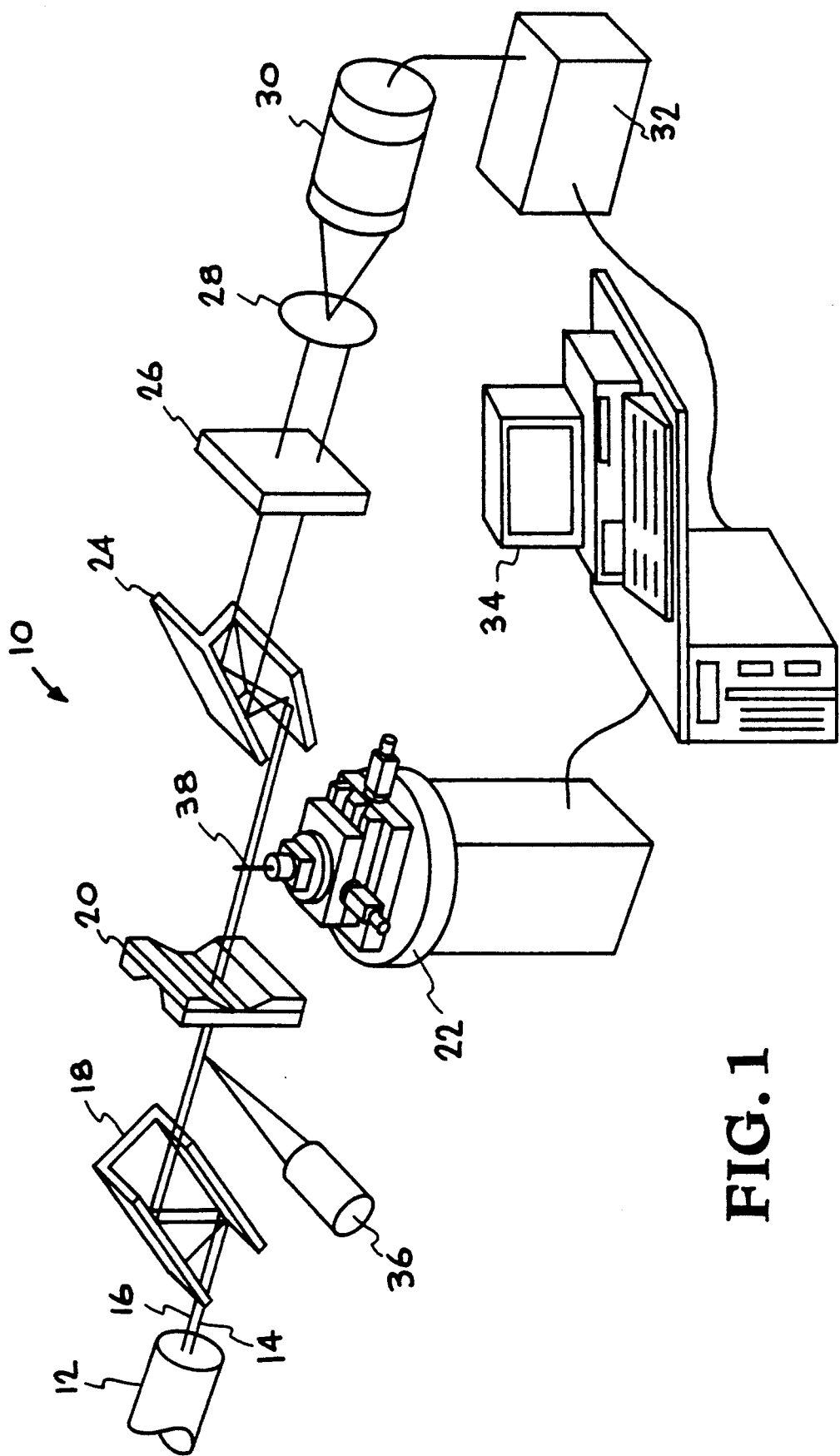
FIG. 1 is a schematic drawing illustrating one embodiment of the x-ray tomographic microscopy system of the invention.

It has now been discovered that the signal to noise ratio and spatial resolution of a computerized x-ray tomographic microscopy system can be improved by incorporating into the system an asymmetric channel cut x-ray image magnifier. Thus, in one aspect this invention pertains to a computerized x-ray tomographic microscopy system utilizing an asymmetric channel cut image magnifier. In another aspect it pertains to the magnifier itself. In a third aspect it pertains to an image magnification process for improving the signal to noise ratio and the spatial resolution of images generated in a computerized x-ray tomographic microscopy system. The system, in its broadest aspect, comprises: a) source means for providing a parallel x-ray beam, b) staging means for staging and sequentially rotating a sample to be positioned in the path of the beam, c) an x-ray image magnifier positioned in the path of the beam downstream from the sample, d) detecting means for detecting the beam after being passed through and magnified by the image magnifier, and e) computing means for analyzing values received from the detecting means, and converting the values into three-dimensional representations.

The image magnification process comprises:

a) providing a parallel x-ray beam, b) passing the beam through a sample as it is being rotated in a predetermined sequence, c) magnifying the beam after it has passed through the sample, d) detecting the beams after they have been magnified, and converting them into electronic values, and e) analyzing the electronic values and converting the values into three-dimensional representations.

The asymmetric channel cut magnifier itself comprises:

a monolithic crystal containing parallel lattice planes having a base with a substantially smooth upper surface, a first plate projecting vertically from said upper surface of said base having a smooth inwardly facing face, a second plate projecting vertically from said upper surface of said base having a smooth inwardly facing face, at least one of said plates being adjustable with respect to the other, said faces of said first and second plates being separated from and asymmetrical with respect to each other, and wherein the lattice planes in each of said plates are parallel to each other.

DETAILED DESCRIPTION OF THE INVENTION

To understand the present invention, knowledge of the principles of x-ray computerized tomography (CT) is helpful.

The x-ray tomographic microscopy (XTM) system of the invention is grounded generally upon the same principles as are used in medical computed tomography. That is, the x-ray attenuation coefficient, $\mu$, at a point $r_{x,y,z}$ in a material can be determined from a finite set of x-ray attenuation measurements (projection data) taken at different angles. The projection data is the transmitted x-ray intensity reaching a position-sensitive detector after passing through the sample. This data, which is directly related to the materials microstructure, is given by;

$$I = S(E) \exp{-\mu(x,y,z,E)dl} \, dE, \tag{1}$$

where $S(E)$ is the energy spectrum of the x-ray source, and $\mu(x,y,z,E)$ is the energy-dependent attenuation coefficient at a single point on the projection. The integral is taken along a straight path dl through the sample.

Because a synchrotron beam can be made nearly monochromatic with photon energy $E_o$, the energy spectrum can be approximated by delta function, and Eq. (1) reduces to the familiar form of the Radon transform, $$\ln I_o/I = \mu(x,y,z,E_o)dl. \tag{2}$$

Measurements of the attenuation through the sample as a function of angle are used to numerically invert Equation (2) to solve for $\mu(x,y,z,E_o)$. The number of angular views considered sufficient for this invention (reconstruction) is approximated, using simple geometric arguments, by $$R\Delta\Theta = W, \tag{3}$$

where R is the maximum outward extent of the sample from the center of rotation, $\Delta\Theta$ is the suggested angular increment, and W is the projection width. A typical value for R with the XTM of the invention is 2 mm, and W is 5 μm. The angular increment sufficient for the reconstruction, using these dimensions, is approximately 0.2°. In practice, however, an increment of 0.5 to 1.0° is usually used because of limited beam time.

The system of this invention has several embodiments. One embodiment of the computerized axial tomography microscopy system of this invention is shown in FIG. 1. As shown, the system 10 comprises an x-ray source 12 which emits parallel beams of x-rays 14, 16. Sequentially positioned in the path of x-rays 14, 16 emanating from the source 12, is a monochromator 18, a collimator 20, a sample stage 22 carrying a sample, a two-stage asymmetric channel cut single crystal beam magnifier 24, a scintillator 26, a lens 28, and a charge coupled device 30. A controller 32 is electronically connected to the charge coupled device 30 for receiving signals therefrom. A computer 34 is electronically connected to the controller 32, and receives signals from it. The sample stage 22 also sends signals to the computer by electronic means.

An incident beam flux monitor 36 is positioned adjacent the monochromator 18 and monitors the x-rays 14, 16 as they exit the monochromator 18.

In operation, parallel beams 14, 16 from the x-ray source 12 is passed through the monochromator 18. This monochromator 18, a double crystal one, selects x-rays in a narrow energy range from the primary beam supplied by the source 12. The beam 14, 16 emitted from the monochromator 18 is passed through the collimator 20 which reduces scatter. From the collimator the beam is passed through a sample 38 positioned on the sample stage 22. From the sample 38, the beam 14, 16 is passed to the two-stage asymmetric channel cut x-ray image magnifier 24. The x-ray image magnifier 24 eliminates scattered x-rays and enlarges the image anywhere from 4 to 25 times, depending on its precise construction. From the magnifier 24, the beam 14, 16 is passed to the scintillator 26, which converts the x-rays to visible light, through the scintillator 26 to the lens 28, and from the lens 28 to the charge coupled device 30.

The charge coupled device 30 records the intensity of the beam 14, 16 (now visable light), and this information is electronically passed to the controller 32 and on to the computer 34.

The sample 38 is sequentially rotated by a stepper motor (not shown) attached to the stage 22.

Light intensity values are recorded by the charge coupled device 30 and passed on to the computer 34 at each stage of rotation of the sample 38. The sample 38 is rotated through 180°. The computer 34 integrates the data obtained and by suitable software programs converts two-dimensional data into three-dimensional images.

Suitable software can be obtained from Lawrence Berkeley Laboratory, Berkeley, California, under the designation Donner Code.

The two-stage asymmetric channel cut x-ray image magnifier 24 comprises two substantially identical single crystals 40, positioned in tandem, one of the crystals being rotated around the axis of the x-ray beams 14, 16 and 90° relative to the other.

As used herein, therefore, the term "two-stage" refers to two of such crystals 40 mounted in tandem.

Figure 2:
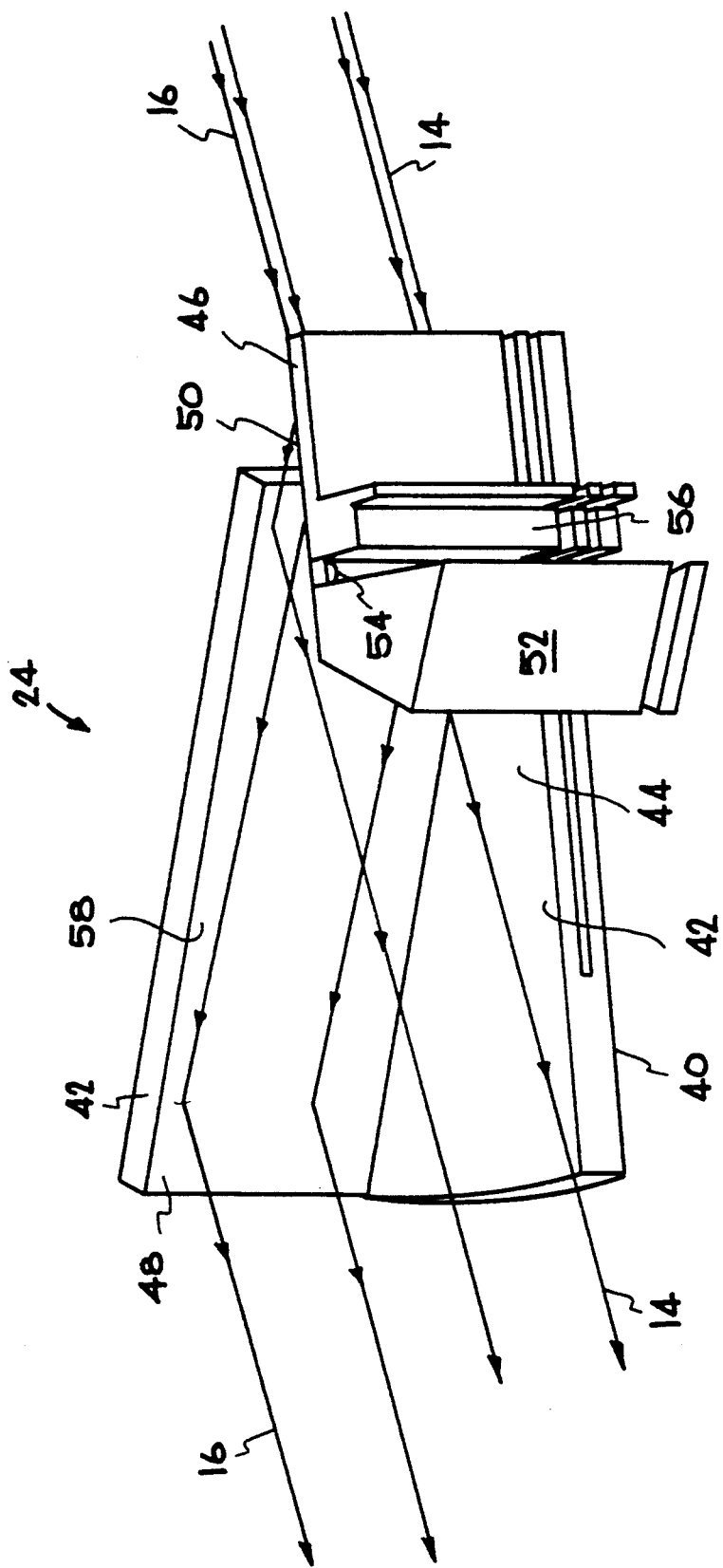
FIG. 2 is a detailed perspective view of the asymmetric channel-cut image magnifier of the invention.

One of the crystals 40 is shown in detail in FIG. 2.

Each single crystal 40 has internal lattice diffraction planes 42, sometimes referred to as Bragg reflecting planes, and comprises a horizontal base 44 which has first and second upright rectangular plates 46, 48 projecting vertically from the top surface thereof. The plates 46 and 48 are cut from the monolithic crystal 40, and have faces which are asymmetric with respect to one another. Plate 46 has an inwardly oriented face 50, a trapezoidal shaped end portion 52, a weak section 54, and a substantially rectangular shaped intermediate section 56.

If desired, a piezoelectric device, not shown, can be attached to the weak section 54, in order that it can be bent in order to correctly align the Bragg reflecting planes 42 in each of the plates 46, 48.

For Proper operation of the magnifier 24, it is essential that the reflecting planes 42 in each of the plates 46 and 48 be close to parallel.

Plate 48 has an inwardly oriented face 58. The faces 50 and 58 are cut asymmetric with respect to the Bragg reflecting planes 42 of the crystal 40 such that the incident angles are not equal to the reflected angles. Beam 14, 16, after having passed through the sample 38 impinge upon the lattice planes 42 of plate 46, and is ultimately diffracted off the lattice planes 42 of plate 48.

The net effect of the diffraction, as seen in FIG. 2, is to increase the magnification of the beam 14, 16 in a single plane by an amount proportional to the ratio of the sines of the reflection angle divided by the incident angle, and to keep the exit beam traveling in the same direction as the incident beams to facilitate alignment.

In the two-stage magnifier 24, two asymmetric channel cut crystals 40 are employed to magnify the image in both planes, i.e., vertical and horizontal. The second crystal is positioned 90° relative to the first.

Figure 3:
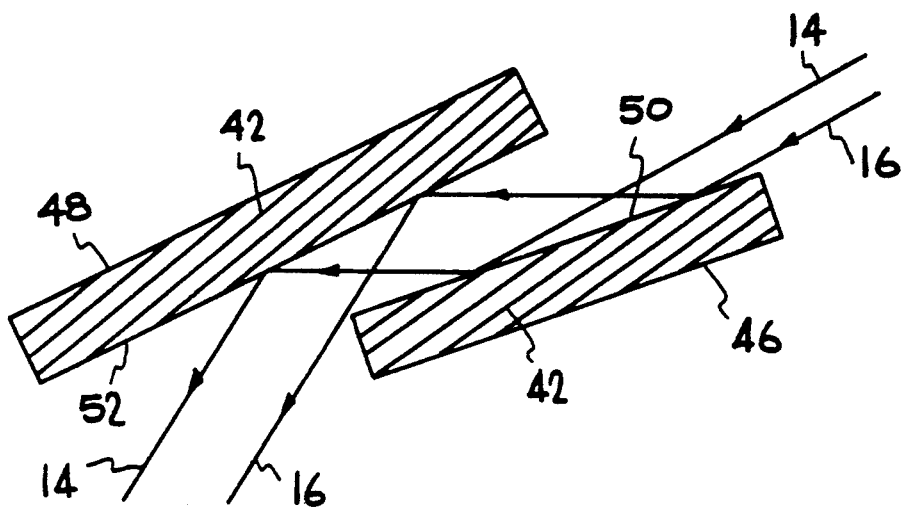
FIG. 3 is a schematic drawing illustrating diffraction of x-ray beams from lattice planes in a silicon crystal.

The optics of the image magnifier crystal 40 are demonstrated schematically in FIG. 3. As shown, incoming parallel x-ray beam 14, 16 is diffracted from the lattice planes 42 in plate 46, travel to plate 48 and are subsequently diffracted from the lattice planes 42 in plate 48.

Figure 4:
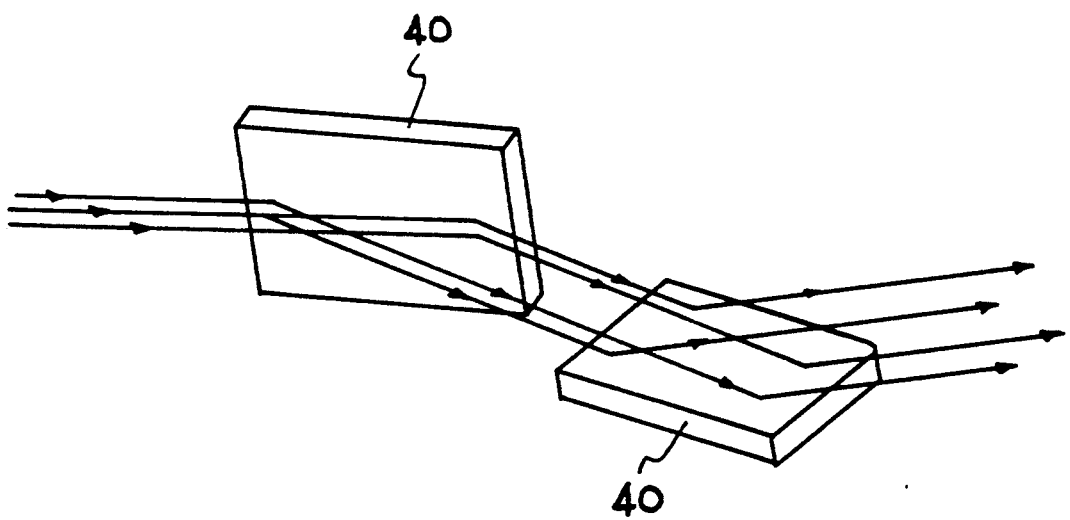
FIG. 4 is a perspective view illustrating the optics of the two-stage asymmetric channel cut image magnifier of the invention.

In FIG. 4 is demonstrated the optics of an x-ray magnifier utilizing two asymmetric diffractions to obtain a two-dimensional magnification of images contained in an x-ray beam. In order to magnify an x-ray beam which contains structure information (such as one containing radiographic images), the beam is successively diffracted from two crystals 40. The plane of diffraction, defined as the plane containing the incoming beam and the normal to the diffracting plane (and also the outgoing beam), for each of the two asymmetric diffractions, must be perpendicular. Hence the first diffraction magnifies the beam horizontally and the second in a perpendicular direction.

The crystal 40 is either Si or Ge, preferably Si.

A preferred magnifier 24 is an asymmetrically cut Si (111) - Si (111) combination in a double crystal configuration. Other combinations which can be used so long as Bragg diffracting conditions are met, include Si (220) - Si (220), Si (400) - Si (400), Si (511) - Si (333), Si (333) - Si (333), Ge (111) - Ge (111), or Ge (220) - Ge (220).

The preferred source of x-rays 12, is an electron storage ring generating synchrotron radiation, because synchrotron x-radiation is very bright, very intense and easily tunable. Most preferred is an electron storage ring like the one located at Stanford Synchrotron Radiation Laboratory (SSRL) and a beamline designated BL-X which is a 30-pole wiggler utilizing Nd-Fe-B magnet materials.

The monochromator 18 is used to select certain energy wavelengths out of the x-ray beam in order to insure that maximum contrast is achieved. Suitable monochromators can be made by those skilled in the art, or can be obtained from the Bede Scientific Instruments Ltd., under the designation x-ray monochromators.

The function of the monochromator is to select a band of x-rays being emitted from the source.

X-rays having energy levels ranging from about 2½ to about 60 KV can be used, but the preferred range is from about 5 to about 20 KV, most preferred about 15 KV.

The use of higher levels of energy, i.e., 60 KV, would require changes in the monochromator 18. Thus, a germanium instead of silicon monochromator would be more efficient.

The monochromator 18 is cooled by water running through the components thereof. Thus, the monochromator is also used to dissapate heat deposited on the crystal as a consequence of the x-rays impinging thereon. The monochromator 18 removes more than 90% of the heat generated by the x-ray beams.

The monochromator must be cooled sufficiently that the rocking curve of the beams is in the range of a few arc-seconds. Thus, the x-ray wavelength must not drift.

Figure 9:
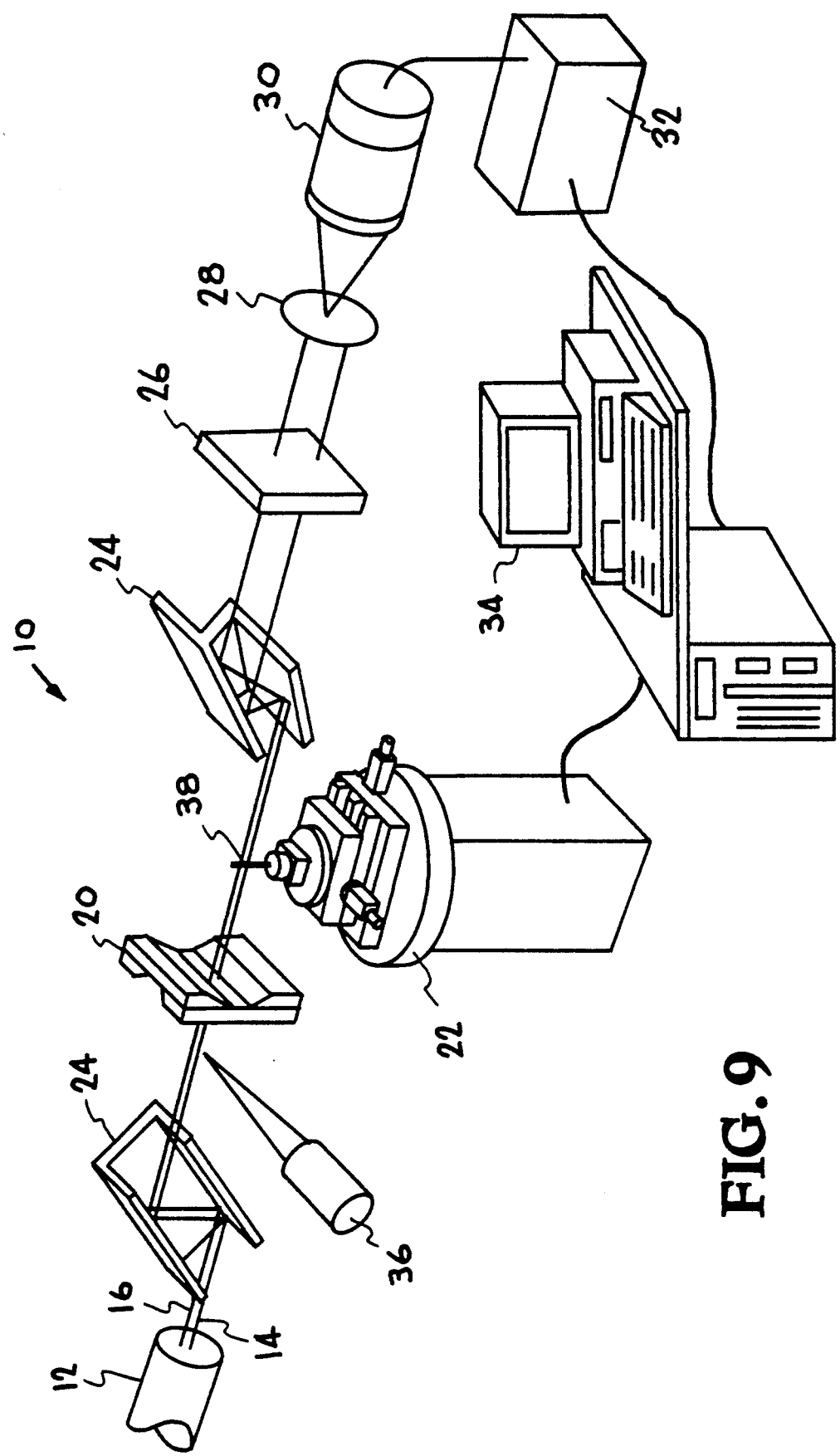
FIG. 9 is a schematic drawing illustrating yet another embodiment of the x-ray tomographic microscopy system of the invention.

If desired, the monochromator 18 can be replaced by another single asymmetric channel cut image magnifier 24. This alternative embodiment is shown in FIG. 9 where the monochromator 18 (as shown in FIG. 1) is replaced by another magnifier 24. The advantage of this is that the beam is made even more parallel and of greater spatial extent and uniformity.

The collimator 20 is a slit type, which allows x-rays 14, 16 emerging from the monochromator 18 to pass through. Because parasitic scatter is a source of blurring, the collimator 20 is located several cm from the sample. The collimator 20 is used to eliminate scatter x-rays from the beam, and to insure that the beams is projected through the sample 38. The collimator is not an essential component of the system, but it is preferred to use one. A suitable collimator is manufactured by the Huber Company, under the trade name Adjustable Slit Collimator.

If the x-ray source 12 is one which emits parallel beam of x-rays having the desired energy levels, then it would also be possible to eliminate the monochromator 18 from the system.

Thus, both the monochromator 18 and the collimator 20 are optional, but preferred components of the system.

After being collimated, the parallel x-ray beam passes through a sample 38 positioned on a stage 22 which contains means for rotating the sample.

The sample stage 22, which provides rotational and translational motion, can be positioned with an accuracy of 0.01° in rotation and 0.1 um in translation. It must be stable within 2 arc-seconds and wobble-free. A suitable sample stage 22 can be obtained from the Klinger Company, and is sold under the designation Stepper Motor.

After passing through the sample, the x-rays pass through the magnifier 24 previously described. The optical principles behind the magnifier are set forth in Rev. Sci. Instrum. 50 (1), January 1979, pps. 26–30, which article is incorporated herein by reference to the extent allowed by law.

To summarize, the magnification (M) achieved is equal to the sine of the ratio of the outgoing angle to the incoming angle, i.e., $$M = (\sin \Phi_{out}) / (\sin \Phi_{in})$$

For maximum performance to be achieved the Bragg planes 42 of the two vertically projecting plates must be close to parallel. The exact relative tilt is determined by the theory of dynamically diffracting perfect crystals (e.g. W. Zachariasen, "Theory of X-Ray Diffraction in Crystals", New York: Wiley 1945) as worked out by R. Nu$\beta$hardt (PhD-Thesis University of Dortmund 1990)..

For practical purposes it has been empirically determined that the outgoing $\Phi_{out}$ and incident $\Phi_{in}$ angles should be greater than 6° and less than 45o The scintillator 26 is used to convert the x-rays to visable light. The scintillator should have flat surfaces polished to within one quarter wave, i.e., it should be optically polished and free of defects. The back side must have an anti-reflective coating on it. Any standard scintillator can be used for this purpose. A particularly useful one is a single crystal one sold by the Harshaw Company under the designation Cadmium Tungstate ($CdWO_4$).

The charge coupled device (CCD) 30 accepts the light from the scintillator 26 in parallel wave fashion. It should be of optical grade and cooled to prevent dark current build-up. It should have no more than 1 charge per second dark current, and its dynamic range should be greater than 1,000. With a wide slowly diverging x-ray beam each pixel of the charge coupled device 30 defines a pencil beam. The CCD pixels measure the intensity of the beam. A suitable CCD device can be obtained from the Photometrics Company, Model No. CH200.

The controller 32 and computer 34 to which signals from the CCD device are passed are both standard items of commerce. The controller 32 can be purchased from the Photometrics Company under the name CC200, while the computer 34 is preferably a Micro Vax II, or III sold by DEC (Digital Equipment Corporation). Any other computer which performs the same function would be suitable.

An alternative to the scintillator 26 used in the system above, is a high resolution phosphor screen. In this embodiment, the image formed on the phosphor screen is projected onto the CCD with an optical lens that has been coated with an anti-reflective film. Any other lens which provides suitable quality can be used.

The beam flux monitor 36 is an optional component of the system of the invention. It is conventionally connected to a single channel analyzer, and simply is used to monitor and count the photons emanating from the beam.

Suitable beam flux monitors can be obtained from the Kevex Corp.

In the practice of the process of this invention, the energy level of the x-ray beam from the synchrotron radiation source can range from about 100 eV to about 100 KeVs, preferably from about 3 KeV to about 40 KeV, and more preferably from about 7 to about 25 KeV. Most preferred is a beam having an energy level of about 15–20 KeV.

Figure 8:
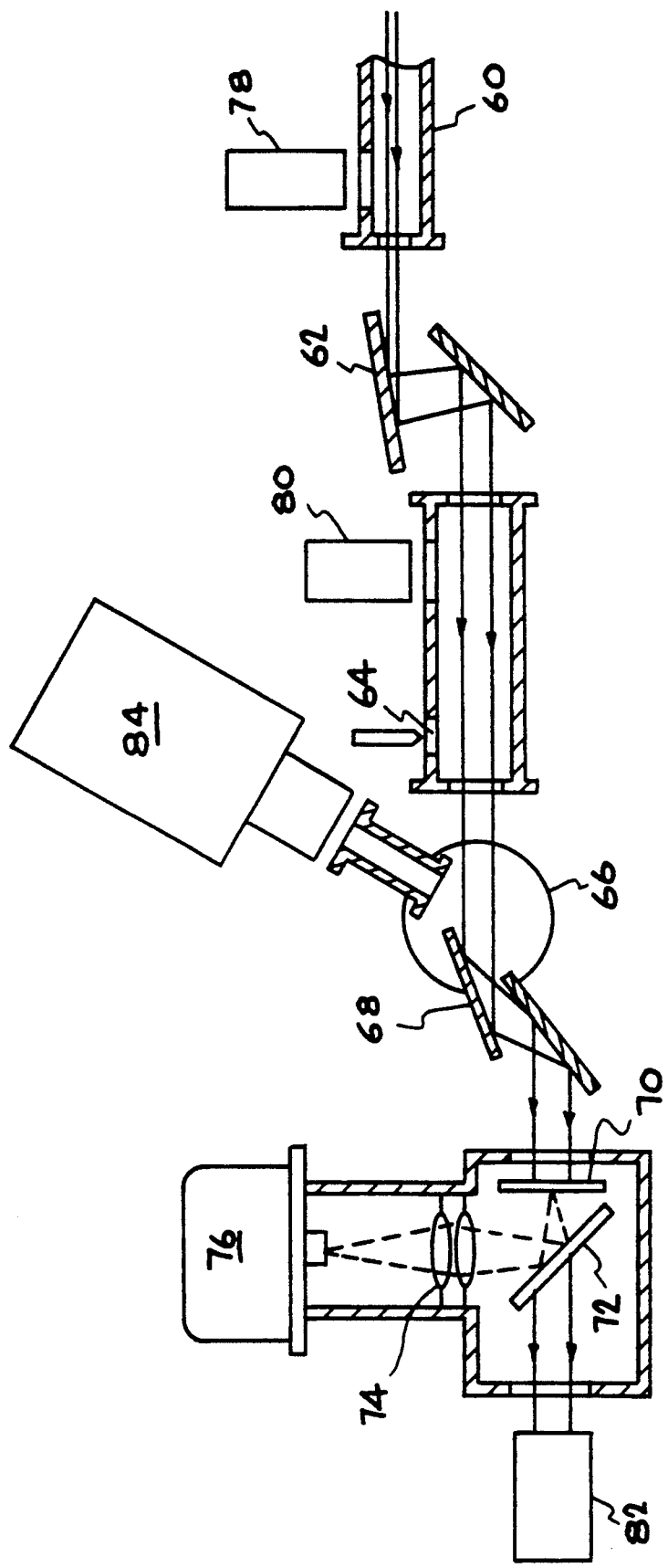
FIG. 8 is a schematic drawing illustrating another embodiment of the x-ray tomographic microscopy system of the invention.

Another embodiment of the system of the invention is shown in FIG. 8.

The system comprises a source of x-ray beams 60, a monochromator 62, a beam shutter 64, a sample stage 66, a magnifier 68, a fluorescent screen 70, an optical mirror 72, a set of lenses 74, a charge coupled device 76, monitor counters 78, 80, and 82, and a solid state detector 84.

The charge coupled device 76 is connected to another apparatus, not shown, which analyses the data obtained and converts it into three-dimensional representations.

This invention will be more fully understood by reference to the following detailed description.

Figure 5A:
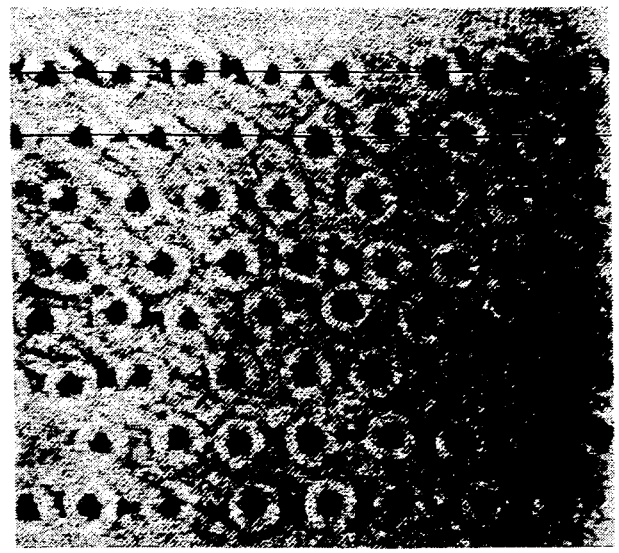
FIGS. 5(a) is a micrograph of a cross section of a sample examined using the apparatus and process of the invention.

A 1.5×1.5×10-mm specimen of an Al/SiC composite was obtained and examined by means of the system of this invention using as an x-ray source the 31-pole wiggler beamline at the Stanford Synchrotron Radiation Laboratory (SSRL). An x-ray energy of 21 keV was selected for good sample transparency and x-ray contrast between SiC and Al. A set of 97 contiguous cross sections of the composite was examined with the system. FIG. 5(a) shows a single slice with a projection width and slice thickness of 5.6 $\mu$m; the spatial resolution is much better than 10 $\mu$. Data was collected with 5-s exposure times at 1° intervals, a much smaller interval than that suggested by the use of Equation (3). This undersampling leads to some blurring of the image; nevertheless, the 32-$\mu$m-diameter graphite cores and surrounding 140-$\mu$m-diameter SiC sheaths are clearly visible. The slight mottling in FIG. 5(a) is caused by either the statistical noise in the image (2%) or actual variations in the materials composition.

Figure 5B:
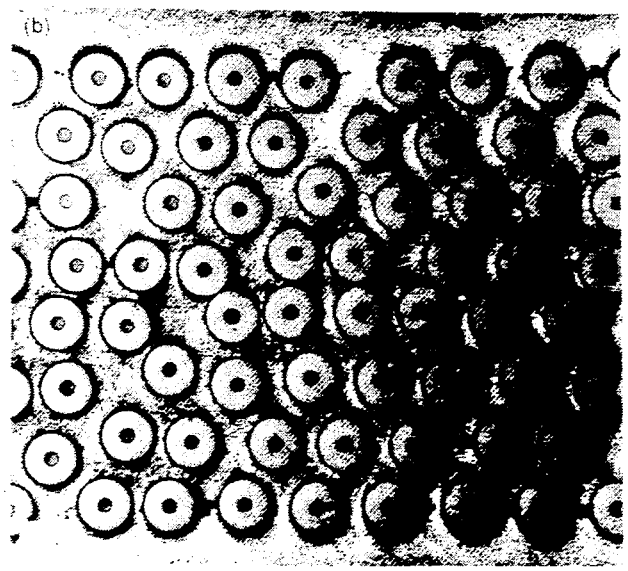
FIG. 5(b) is an optical micrograph of similar sample for comparison.

Cracks running longitudinally in the plane of the fiber plies are evident in FIG. 5(a). These cracks, which do not penetrate the fibers, are similar to those observed in polished sections of the composite [FIG. 5(b)] and may, therefore, be a result of processing. This material is fabricated by means of a plasma-spray technique and is consolidated at high temperatures. It is possible that mismatches in thermal-expansion coefficients may create residual stresses that open these cracks during cooling, or that the material is not being completely surface relief and plastic flow of the matrix during polishing have apparently obscured the interfacial cracks that are observed in FIG. 5(a). This result highlights one advantage of the process of the invention over conventional metallography.

Figure 6A:
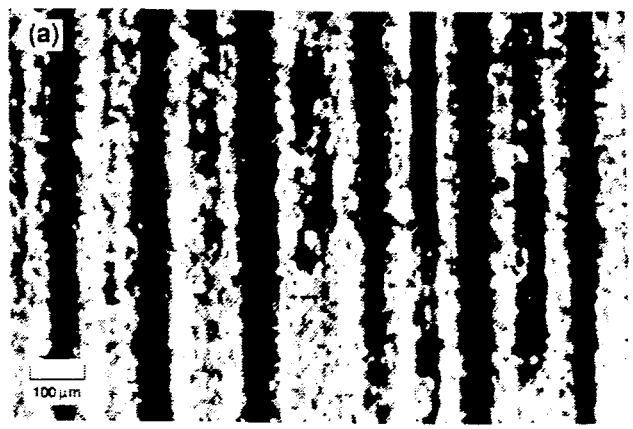
FIGS. 6(a) and (b) are micrographs of planar cuts through the same sample as FIG. 5.
Figure 6B:
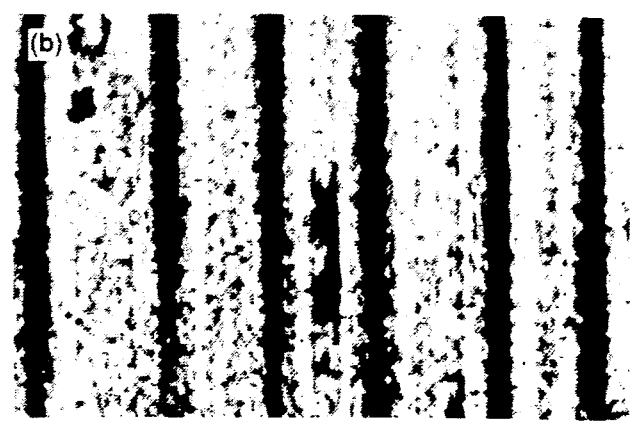

FIG. 6(a) is a planar cut through the same sample as in FIG. 5, but parallel to the fibers. In this ply, the fibers are regularly arranged, and few cracks are present. FIG. 6(b) is a similar plane taken through a ply that is heavily populated with cracks. FIG. 6 demonstrates that the cracks tend to run along the fiber-matrix interface and between nearest-neighbor fibers rather than across the plies of the composite.

Figure 7:
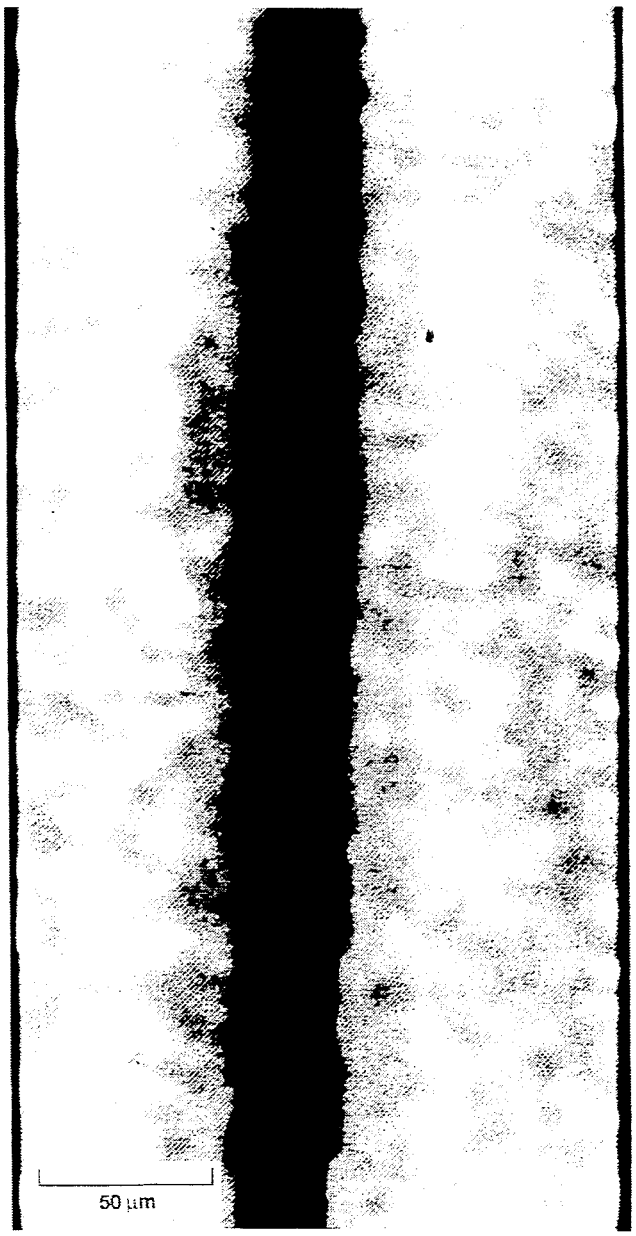
FIG. 7 is an enlarged micrograph of a planar cut through the same sample as FIG. 6(b) at a different location than shown in FIG. 6(b).

FIG. 7 is a view of a single fiber that shows the graphite core and SiC sheath surrounding it. The change in columnar SiC subgran size produced during the growth of the sheath is evident, as is the SCS-8 coating in the final few micrometers near the Al interface.

The application of x-ray tomographic microscopy (XTM) to the study of two Aluminum composites, one with $Al_2O_3$ whiskers only 2-4 $\mu$m diameter (sample 1), the 2) is described below. As will be shown, using XTM enabled the imaging in sample 1 of the clustering of intermetallic precipitates. In sample 2 the individual fibers were resolved. Furthermore, by exploiting the elemental sensitivity of XTM, the precipitates of different intermetallic phases in the composite matrix and correlated them with structures seen on optical, back-scattered electron (BSE), and wavelength dispersive (WDS) micrographs were imaged. The power of XTM as a high-resolution and nondestructive 3-D imaging method sensitive to elemental distribution, density changes, and binding state fluctuations becomes evident from these results. Measurements on sample 1 were performed on the 1 pole wiggler beamline 10-2 of SPEAR at SSRL (Stanford) employing a pair of symmetrically cut (220) Silicon crystals as monochromator and a Peltier-cooled CCD detector. Sample 2 was investigated on the bending-magnet beamline of the Two-Axis-Diffractometer, U. Bonse and K. Fischer, Nucl. Instr. Meth. 190 (1981), 593, at DORIS of HASYLAB (Hamburg) employing a cryogenically cooled CCD and the crystal magnifier described below and shown in FIG. 8. Furthermore, a special Germanium monochromator combining an asymmetrically cut (511) crystal with a symmetric (333) crystal, U. Bonse et al, HASYLAB Jahresbericht (Desy, Hamburg, 1988), p. 395, was optionally used. While preserving the nondispersive double crystal setting, the choice of the homologous 5 reflections (511) and (333) provides different crystallographic orientations for the crystals so that the occurrence of Laue spots is minimized. The asymmetry of the first crystal increases the acceptance of radiation from the SR source and at the same time reduces the divergence of the beam incident on the sample which improves spatial resolution.

While the wiggler beamline is superior with respect to intensity, the more elaborate monochromator at DORIS allows better control of vertial beam size and divergence and of harmonic content. A monochromator optimized for XTM is expected to produce a beam with <0.2 mrad divergence, 1 to 5 mm² cross section, wide energy tunability at <0.02% bandwidth and total harmonic content less than 0.1%. Typical storage ring operation parameters were 3.3 GeV, 30 mA, 12 hours lifetime at SPEAR Harmonic suppression/selection of the FIG. 8 system is achieved by suitably detuning the component crystals of MC 62 with respect to each other. For this to function in a proper way, the first crystal of MC 62 is internally water-cooled, U. Bonse et al, HASYLAB Jahresbericht (DESY, Hamburg, 1986), p. 395, in order to maintain its undeformed perfect crystal state under the unavoidable heatload delivered to it by the primary beam. The energy dispersive solid state detector 84 is used for monitoring the harmonic content and for energy calibration.

The sample S is mounted on a rotary stage 66 capable of 360 degrees rotation at 0.001 degree minimum increment. Typical angular increments between individual Projections varied from 0.25 to 3 degrees depending on the required spatial resolution. For taking empty-beam references, the sample is shifted out of the beam in a direction parallel to its rotation axis. When the primary beam is not stationary, it is necessary to have references taken frequently. In order not to spend too much time removing the sample and setting it back, a device was constructed capable of withdrawing it at a speed >4 cm/s. After the reference has been taken, the sample is placed back into the beam at the same speed. The original sample position is reproduced to better than 1 micron accuracy. This is an important feature in order not to deteriorate spatial resolution through uncontrolled positional changes of the sample between exposures.

Presently available CCD detectors both are damaged when exposed to x-rays and become transparent at photon energies above 10 keV. Hence x-ray-to-light conversion by a fluorescent screen or by a single-crystal scintillator is necessary. The advantage in using a single-crystal is that scattering of light inside the scintillator is negligible whereas with a polycrystalline screen light scattering is an additional cause of limited spatial resolution. On the other hand, a fluorescent screen is usually 10 to 50 times more efficient than the single crystal scintillator.

The conversion of x-rays to light allows the use of straightforward optical light magnification to lessen the resolution requirements imposed on the CCD. Problems of limited spatial resolution inherent in x-ray-to-light converters are overcome by employing x-ray-optical magnification, U. Bonse et al, HASYLAB Jahresbericht (DESY, Hamburg, 1988), p. 469, and U. Bonse et al, HASYLAB Jahresbericht (DESY, Hamburg, 1989), p. 557, provided by twofold asymmetric Bragg reflection, the principle of which is explained by FIG. 2. The crystal magnifier consists of a grooved crystal with walls oriented at opposite asymmetry with respect to the reflecting Bragg planes. A suitable crystal is one which uses 220 (440) reflections with x-rays of about 9 keV (18 keV) energy, respectively. With this crystal, linear x-ray optical magnification in the range of two- to tenfold is achieved, the actual magnitude depending on the energy of the radiation used.

Two kinds of converters, a $CdWO_4$ single crystal plate 0.5 mm thick and an Eu-doped $Y_2O_2S$ fluorescent screen about 40 $\mu$m thick have been used. While the fluorescent screen was - depending on photon energy—up to 15 times greater in fluorescence than the single crystal plate, the single crystal provided considerably better spatial resolution.

Projection of the fluorescent light image onto the CCD is achieved by employing either a single standard photographic lens with 50 mm focal length or a pair of such standard lenses, one with 50 mm and the other with 20 mm focal length in telefocal geometry. With the pair of lenses, a light-optical magnification of 2.4 is obtained. With the single lens, a magnification up to about 8 is easily feasible although rarely needed. With a lens system which is custom manufactured to optimally image the screen onto the CCD, optical magnifications up to tenfold at spatial resolution of 2-3 $\mu$ can be achieved, although such resolution requires no image degradation in the scintillator screen. This is possible only below 10 keV photon energy. At higher energy the conversions of x-rays to visible light is stretched out over a depth range which is likely to exceed the depth of focus range of the lens.

Combining the x-ray optical with the light optical method of enlarging the projections, an overall magnification of up to 100 between the sample and the CCD is possible. At this magnification, to detect in the sample a detail of 1 $\mu$m size requires a CCD pixel size of less than 50 $\mu$, which is easily obtained with commercially available CCD's. On the other hand, the maximum magnification is likely to be difficult to work with and in many cases will limit the size of the field of view unduly. These considerations, when taken together, indicate that CCD pixel sizes of the order of 5 to 20 $\mu$m are probably best for XTM, with larger formats being desirable for imaging wider fields of view. Accordingly, the CCD types shown in Table 1 have been employed.

TABLE 1

| Type | CCD Detectors Used for XTM | |
|---|---|---|
| | Format | Pixel Size |
| Thomson CSF TH7882CDA | 384 × 576 | 23 $\mu$m × 23 $\mu$m |
| Texas Instruments 4849 | 390 × 584 | 22 $\mu$m × 22 $\mu$m |
| Kodak KAF-1400 | 1320 × 1035 | 6.8 $\mu$m × 6.8 $\mu$m |

The CCD with the smallest pixel size provides the highest resolution. However, with this CCD the maximum number of electrons that can be stored in a single pixel is only 1/5 that for the other two CCD's. Hence the smaller pixel size implies an accordingly smaller dynamic range of about $5 \times 10^3$. This is to be compared to about $5 \times 10^4$ for the CCD's having larger pixels. Hence, whenever a high dynamic range combined with the use of small-pixel CCD's is required, multiple exposures per radiograph are unavoidable.

At SSRL data readout and processing was performed on a Microvax II and a VaxStation 3200 equipped with total CPU memory of 32 Mb and total disk space of about 3 Gb. A typical run for sample 1 included 365 radiographs each 736 columns wide and 421 rows high on the KAF-1400 CCD, measured at 1 degree angular increments. Slightly more than half of the radiographs were references taken of the empty beam. With the wiggler source, employing 2.4x optical magnification and the above CCD, exposure times per radiograph ranged from 5 to 15 sec., with the longer exposure related to the beam decay during the scan.

Allowing also for time spent on readouts and mechanical motions of the sample, a typical run required from 2 to 5 hours of beam time. Between runs, a quick reconstruction of a single slice was made for survey purposes, using reduced data sets of only 100 columns obtained by averaging. Complete data sets took roughly 20 min per reconstructed slice. All reconstructions were performed using the method of filtered back projections, G. T. Herman, "Image Reconstruction from Projections: The Fundamentals of Computerized Tomography". (Academic Press, New York, (1980) and R. H. Huesman et al, "Donner Algorithms for Reconstruction Tomography", (Lawrence Berkeley Laboratory, University of California, October, 1977).

The minimum amount of data one has to cope with in XTM may be estimated as follows: Assume a sample of width W and height H which is imaged at spatial resolution $\Delta$. We shall require that the spatial resolution of the 3-D reconstruction is also $\Delta$. This requirement determines the number, N, and size (R rows times C columns) of the radiographs to be collected. The size is H/$\Delta$ rows (each corresponding to one reconstruction slice in the 3-D output image) and W/$\Delta$ columns (each representing the sums of the absorption along paths through the sample at a given distance from the rotation axis). We must take N=$\pi$C/4 such radiographs at angular increments of 180/N degrees. The resulting data contains N.R.C voxels which require a minimum of N.R.C.B bytes of storage if B bytes are used to store each voxel. In practice, 20 to 100% more data is collected because of the need to collect reference and dark images in order to compensate beam instability, CCD background and CCD nonuniform pixel sensitivity. Each reconstruction slice uses at least N.C.B bytes of raw data to produce $4C^2$ bytes of real-valued output. Performing reconstructions for the entire 3-D volume produces $4R.C^2$ bytes to be dealt with during 3-D rendering.

As an example, consider a cylindrical sample of 1 mm in diameter and 0.5 mm high which is imaged at 3 micron spatial resolution: Each radiograph will have 167 rows and 333 columns. Two hundred sixty-two radiographs must be taken with the sample rotated 0.7 degree between each exposure. The resulting data consists of about $1.5 \times 10^7$ voxels. Assuming the use of the KAF-1400 CCD which collects 12 bits of data (a dynamic range of about $4 \times 10^3$) stored in 2 bytes of memory, about 30 Mbytes of data must be stored. Each reconstruction slice uses about 174 kbytes of input to produce about 444 kbytes of output. Reconstruction of all the data produces about 74 Mbytes of output to be rendered into a 3-D image.

The assumed definition of resolution reflects a very conservative point of view. It should not be confused with the detectability of smallest-size objects. It was found in practice, that objects considerably smaller than the defined resolution limit are detectable under conditions of good contrast The correct treatment of resolution must be based on the concept of modulation transfer function (MTF), R. K. Swank, Appl. Opt. 12 (1973), 1865, which correctly accounts for the inherent link between the smallest size of a detectable object and its contrast.

It may also be pointed out that the amount of data to be measured and handled does not primarily depend on the spatial resolution but rather more simply on the number of voxels which must be examined together with what dynamic range is required in the final image. On the other hand, given a fixed sample volume, the amount of data to be measured scales with the third power of $1/\epsilon$, $\epsilon$ being the smallest distance to be resolved. Hence when going to higher resolutions it becomes more important to limit the sample volume to its absolute minimum. At the same time, especially when employing CCD's with smaller and hence many more pixels, it appears very important to develop faster on-chip readout techniques and to provide storage media of several tens of Gb capacity. For fast rendering of the reconstructed 3-D image, the data of all pixels have to reside in CPU memory. This means the size of the memory should be on the order of 80 Mb and more.

Figure 10:
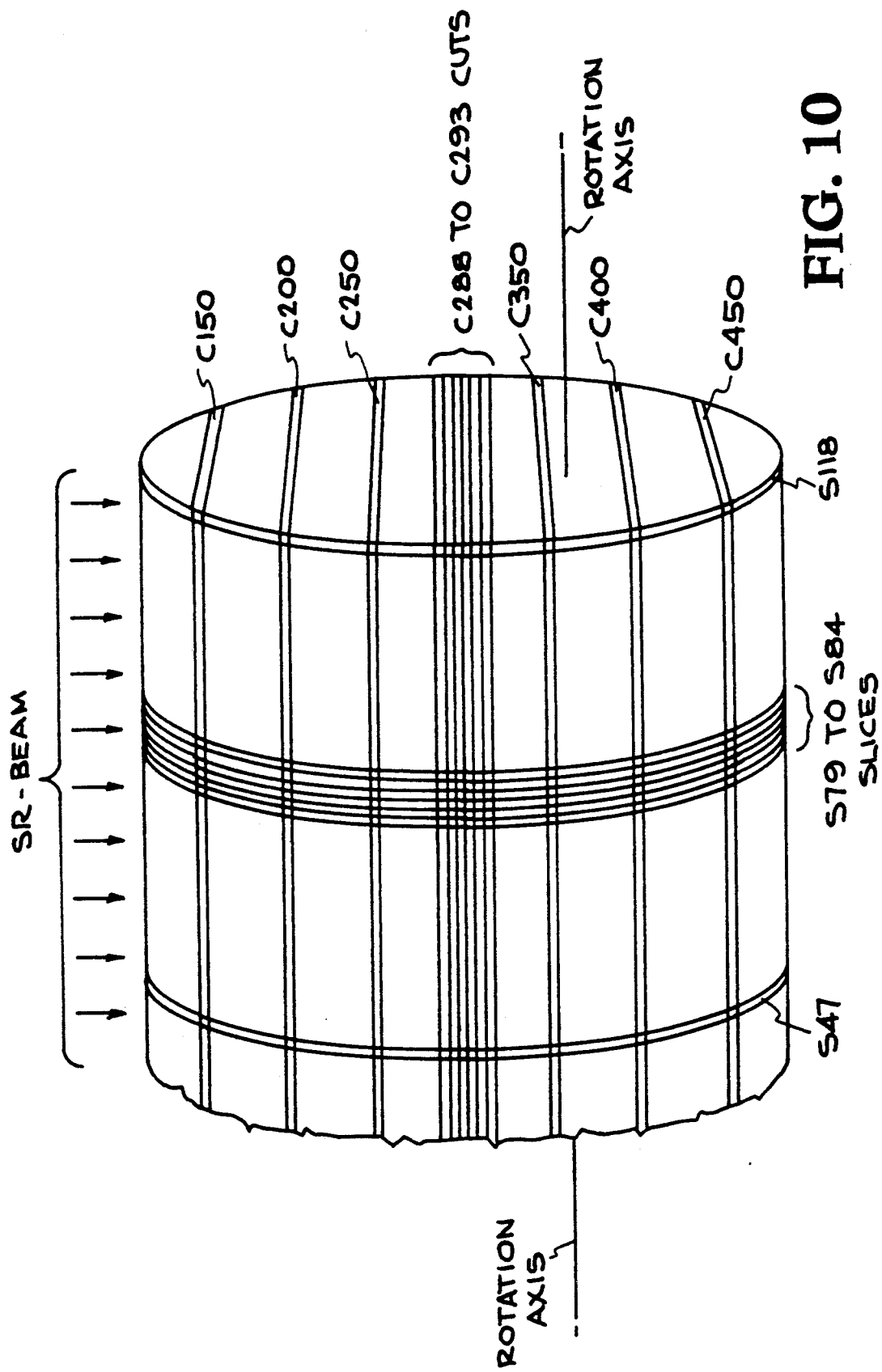
FIG. 10 is a perspective view of a sample showing identification of x-ray tomographic microscopy (XTM) images, which are designated slices (S) if oriented at right angle, and cuts (C) if oriented parallel to the rotation axis.

In the following discussion of the XTM images of sample 1, we will refer to 'cuts' and 'slices' as illustrated in FIG. 10. As is seen, all voxels of a given slice are related to each other through the same reconstruction calculation. Voxels of different slices are completely independent from each other. In contrast to this, voxels of a given cut are reconstruction-related only if they belong to the same line, where line means a line normal to the rotation axis. It is important to keep these relationships in mind when discussing the possibility that artifacts are generated by the reconstruction algorithm.

Figure 11:
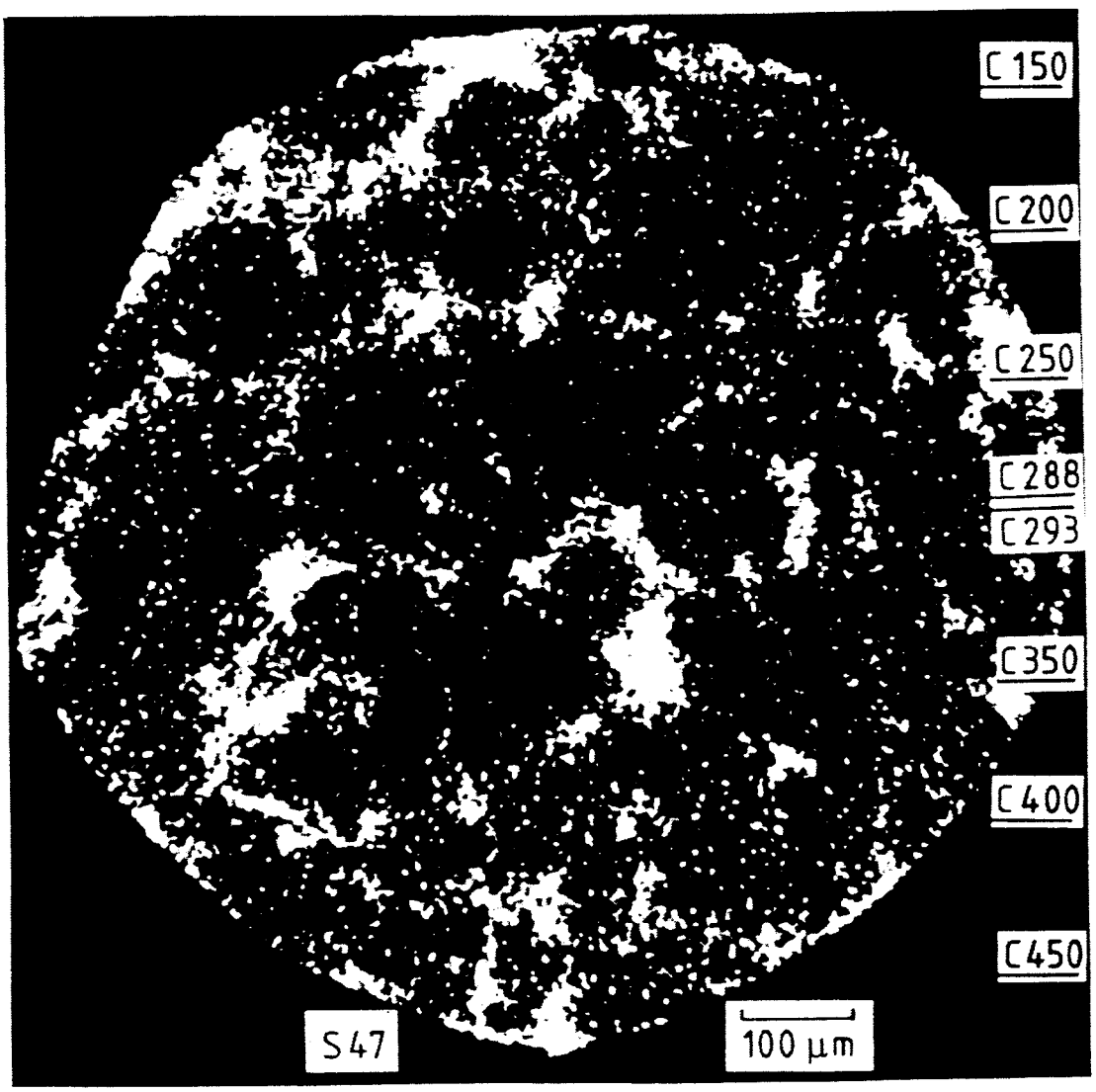
FIG. 11 is a micrograph of the computerized representation of XTM-slice S47 (FIG. 10) taken at 20 kV of a sample which is an Al-composite reinforced by $Al_2O_3$ fibers 2 to 4 μm in diameter and 50 to 80 μm in length. The XTM images have sufficient elemental sensitivity to distinguish between different crystallographic phases, as demonstrated by the following electron micrographs.

FIG. 11 shows the XTM image of slice S47 of sample 1 (FIG. 10) taken at 20 keV. The almost cylindrical shape of the sample is recognizable. Bright areas in the picture correspond to higher absorption caused by alloy-phases in the Al matrix. The phases contain elements with z-values larger than that of Al.

At first sight, the regions of strong absorption seen in FIG. 11 appear to form a three-dimensional 25 network with an average mesh size of roughly 150 μm. However, there is another net, less absorbing than the first one, and featuring a much smaller mesh size of about 15 μm. From a closer inspection of FIG. 11 we find that the strongly absorbing regions are just clusters of meshes of small cell size, i.e., there is only the smaller net which, however, has nonuniform density. (Circles around the center of rotation seen at the lower left are artefacts due to defective pixels).

Figure 12:
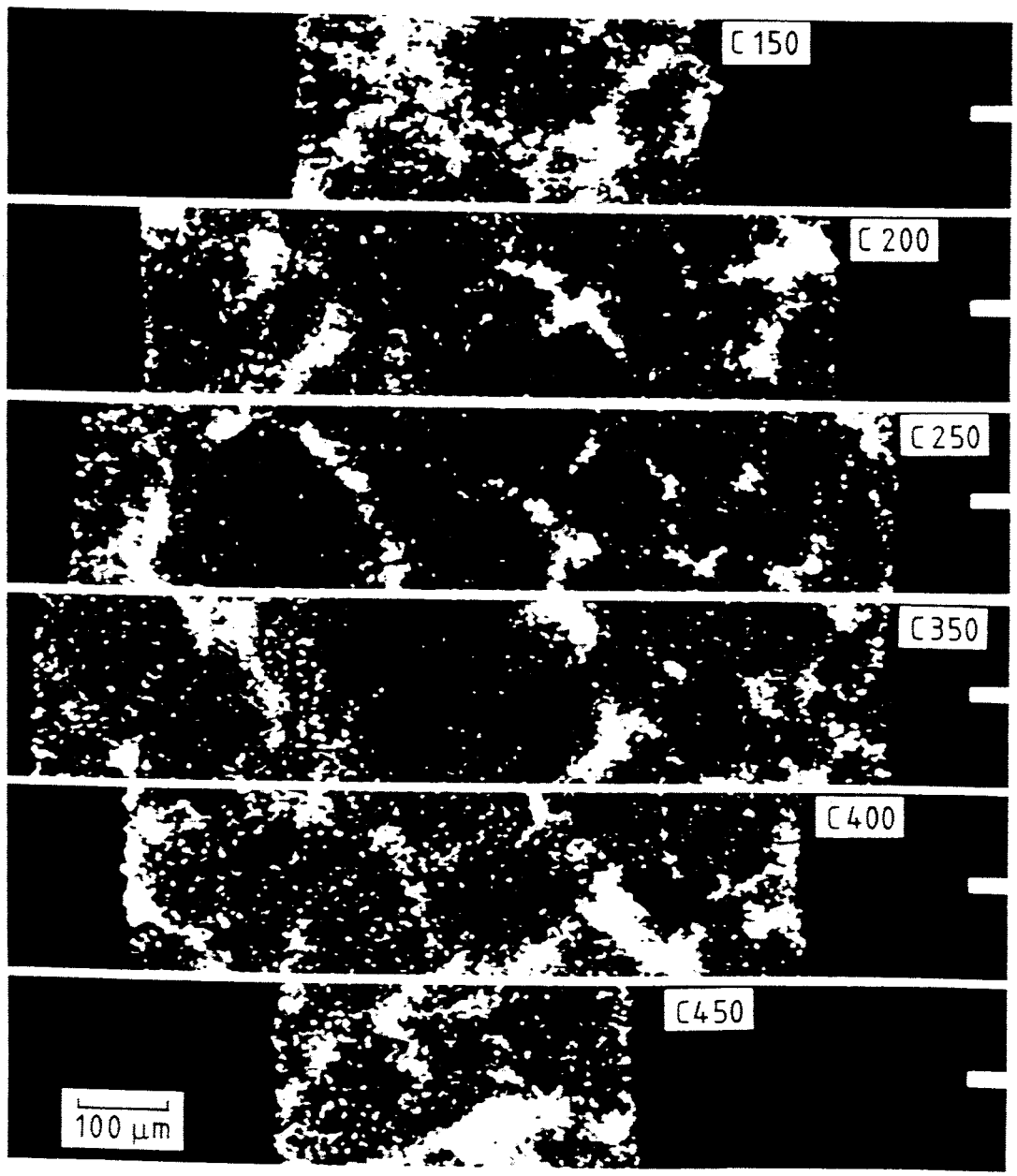
FIG. 12 is a micrograph of a computerized representation of XTM cuts C150 to C450 of the sample of FIG. 11, oriented as illustrated in FIG. 10, i.e., at right angle to the slice of FIG. 11.

FIG. 12 shows cuts C150, C200, C250, C350, C400, and C450, all taken at right angle to FIG. 11. The locations where these cuts have been made are indicated in FIG. 10 and also on the right side of FIG. 11 in order to see easily the correspondence of the top lines of each cut with the structure seen in FIG. 11. Evidently the structure is the same in both directions, meaning that the network has no noticeable texture.

The aluminum matrix is type KS 1275 AlSi$_{12}$CuMgNi from Kolbenschmidt AG, Neckarsulm. Its stated overall composition is 11 to 13% Si, 0.8 to 1.5% Cu, <1.3% Ni, <0.7% Fe, <0.2% Ti, <0.3% Mn, 0.3% Zn, and the balance Al. The material is normally used for pistons of diesel engines. The fiber reinforcement improves the material strength at higher working temperatures.

Figure 13A:
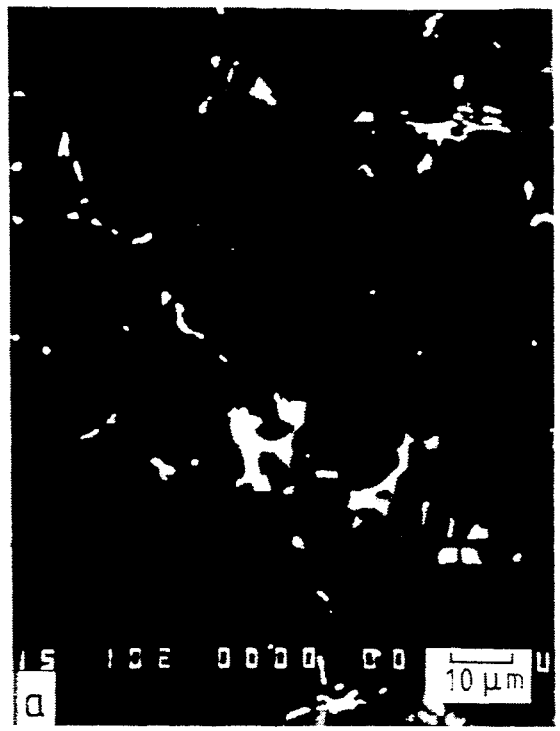
FIG. 13(a,b) is a micrograph illustrating identification of alloy phases in the FIG. 11 sample. a: BSE-map showing three different types of phases, 1 (light), 2 (grey), 3 (dark grey). b: contours of different phases and their numbering.
Figure 13B:
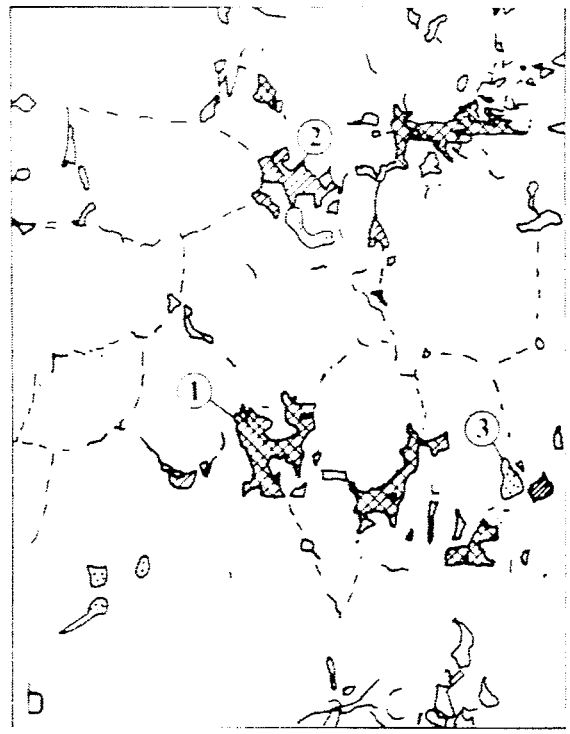
Figure 14:
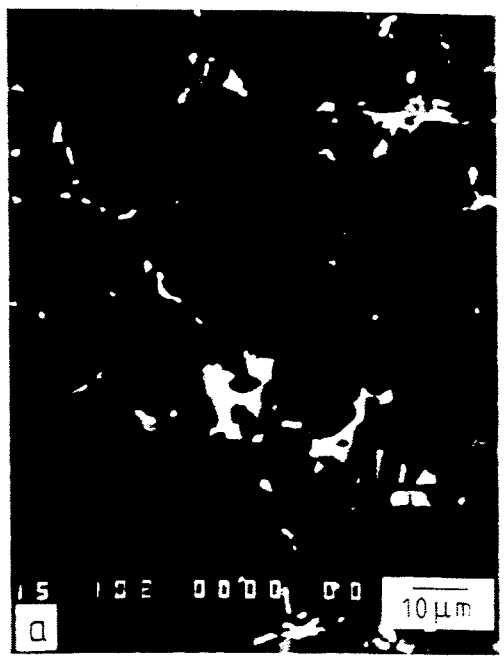
FIG. 14(a,b,c,d) is a series of micrographs illustrating identification of alloy phases in the sample described in FIG. 11. a: BSE-map as FIG. 13. b: Fe-WDS-map. c: Si-WDS-map. d: 0-WDS-map.
Figure 14:
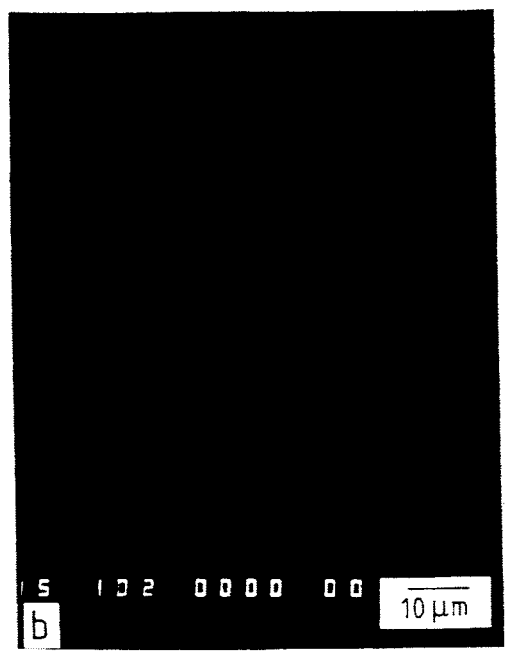
Figure 14:
Figure 14:
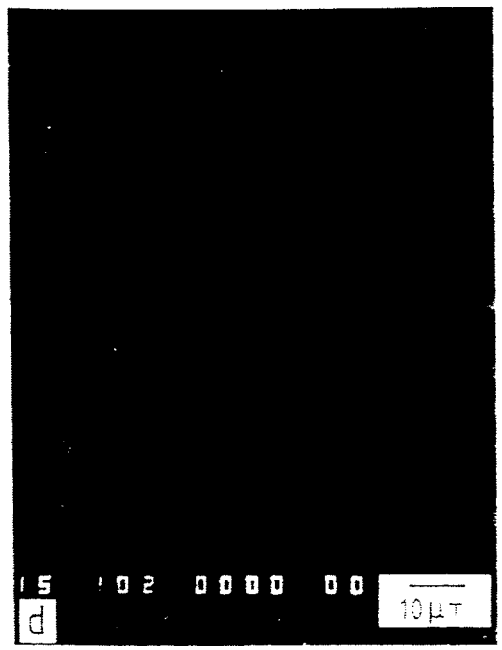

The elements present in the alloy phases have been identified by inspection of back-scattered electron-micrographs (BSE) and wavelength-dispersive spectrometer-maps (WDS), examples of which are shown in FIG. 13 and FIG. 14. On the BSE micrograph FIG. 13a there are three types of phases distinguished, 'light', 'grey', and 'dark grey', respectively. The different types are labeled 1, 2, and 3 in FIG. 13b in which the pertinent contours of FIG. 13a have been redrawn in order to facilitate the recognition of the different phase types. From WDS-maps like those shown in FIG. 14b, 14c, and 14d for Fe, Si, and O, respectively, and other WDS-maps including Ni and Mg, it is found that phase 1 (light) contains Ni, Fe, Si, and Cu. Phase 2 (grey) contains Si, Mg, Ni, Fe, and Cu. Phase 3 (dark grey) is made up mostly of Si. Furthermore, strong evidence is obtained from the BSE-micrographs and WDS-maps that all three phases interconnect to form a three-dimensional network with an average mesh size of about 15 μm. This could correspond to the smaller net observed on the XTM micrographs FIGS. 11, 12, 15 and 16.

Figure 17:
FIG. 17 is an optical micrograph of the surface of the sample described in FIG. 11.

The Al$_2$O$_3$ fibers are seen as black spots on the BSE-micrographs in FIGS. 13a and 14a. They match perfectly with light spots on the Oxygen WDS-map shown in FIG. 14d. The fibers are also clearly seen in the optical micrograph of FIG. 17. Most Al$_2$O$_3$ fibers are oriented normal to the plane of FIG. 17. The result of a determination of all the compositions, i.e., of the matrix, of the phases 1,2,3 and of the fibers performed by x-ray fluorescent analysis (XFA) is given in Table 2. Because of the smallness of the phase grains the amount of Al is overstated in Table 2.

TABLE 2

Approximate Composition of Sample 1 in Weight % (W %) and atomic % (A %) as Determined by Electron Microprobe Analysis

| Element | Matrix | | Light Ph. | | Grey Ph. | | Dark Ph. | | Fiber | |
|---|---|---|---|---|---|---|---|---|---|---|
| | W % | A % | W % | A % | W % | A % | W % | A % | W % | A % |
| Oxygen | — | — | — | — | — | — | — | — | 43 | 56 |

TABLE 2-continued

Approximate Composition of Sample 1 in Weight %
(W %) and atomic % (A %) as Determined by Electron
Microprobe Analysis

| Element | Matrix | | Light Ph. | | Grey Ph. | | Dark Ph. | | Fiber | |
|---|---|---|---|---|---|---|---|---|---|---|
| | W % | A % | W % | A % | W % | A % | W % | A % | W % | A % |
| Magnesium | .3 | .4 | — | — | 19.3 | 23 | .3 | .4 | — | — |
| Aluminum | 98 | 98 | 64 | 78 | 42 | 44 | 31 | 32 | 55 | 42 |
| Silicon | 1.6 | 1.5 | 1.7 | 2.0 | 27 | 27 | 68 | 67 | 1.9 | 1.4 |
| Iron | — | — | 7.5 | 4.4 | 2.1 | 1.1 | — | — | — | — |
| Nickel | — | — | 25.6 | 14.4 | 8.5 | 4.0 | — | — | — | — |
| Copper | — | — | 1.0 | .6 | 1.1 | .5 | — | — | — | — |

Al-rich alloy systems including the elements listed in Table 2, i.e., Mg, Si, Fe, Ni, and Cu, are known, "Equilibrium Diagrams of Aluminum Alloy Systems", Aluminum Development Association, 33 Grosvenor Street, London, W1, U.K., The kynoch Press, Birminghan, 1961, to contain the intermetallic phases shown in Table 3. From the known structure of these phases we have calculated their densities as listed in column 3 of Table 3. Using

TABLE 3

Properties of Components of Al-rich Alloy Systems
Containing Mg, Al, Si, Fe, Ni, and Cu

| Component [14] | Structure [15] | Density [g/cm$^3$] | Absorption 20 keV | | Occurrence Phase | | |
|---|---|---|---|---|---|---|---|
| | | | [1/cm] | relat. | 1 | 2 | 3 |
| Al | | 2.70 | 9.11 | 1 | | | |
| Si | CF8 | 2.33 | 10.15 | 1.11 | | | x |
| Mg$_2$Si | CF12 | 2.00 | 6.56 | 0.72 | | x | |
| Al$_{3.2}$Fe | mC102 | 3.81 | 46.30 | 5.08 | x | x | |
| Al$_3$Ni | oP16 | 3.98 | 61.88 | 6.79 | x | x | |
| Al$_3$Ni$_2$ | hP5 | 4.76 | 97.65 | 10.72 | x | | |
| Al$_2$Cu | tI12 | 4.36 | 86.59 | 9.50 | x | | | the elemental mass absorption coefficients of reference, E. F. Plechaty et al. "Tables and Graphs of Photom Interaction Cross Sections from 0.1 keV to 100 MeV derived from the LLNL Evaluated Nuclear Data Library," 1981, UCRL-50400, Vol. 6, Rev. 3, we determined the linear and relative absorption coefficients of all components (columns 4 and 5 of Table 3). Because of the low solubility of Si in Al and the presence of a considerable amount of Mg, m ost of the Si is present in the component Mg$_2$Si. Since there is not enough Mg to bind all of the Si, the rest is found as a separate component consisting of the element Si, which we believe is identical with our phase 3 seen in FIG. 13 and FIG. 14c. Considering the composition of phase 2 we find that it is very likely made up of Mg$_2$Si plus Al$_3$Ni and a small fraction of Al$_{3.2}$Fe. Similarly, we conclude that phase 1 consists of the last four components listed in Table 3. The important point is that, according to the values found in Table 3, the absorption is high for phase 1, medium for phase 2 and not much different from that of the Al matrix in the case of phase 3. Therefore, in XTM micrographs we expect to see essentially three main levels of contrast. This is in agreement with the observation if we interpret the bright regions to be mostly phase 1 and the less bright net structure to consist of phase 2. Because of its low contrast, phase 3 is not likely to be seen at all at these size scales.

Figure 15:
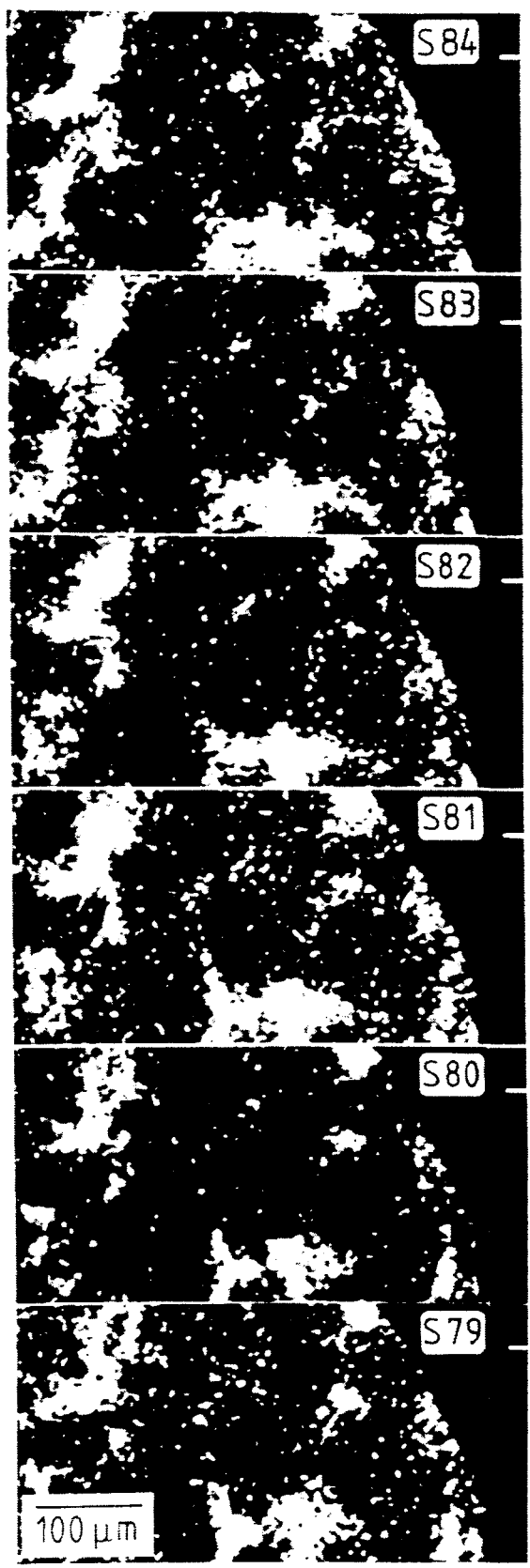
FIG. 15 is a micrograph of a set of six neighboring XTM-slices S79 to S84 (FIG. 10) of the sample described in FIG. 11 illustrating the continuity of the network between slices.
Figure 16:
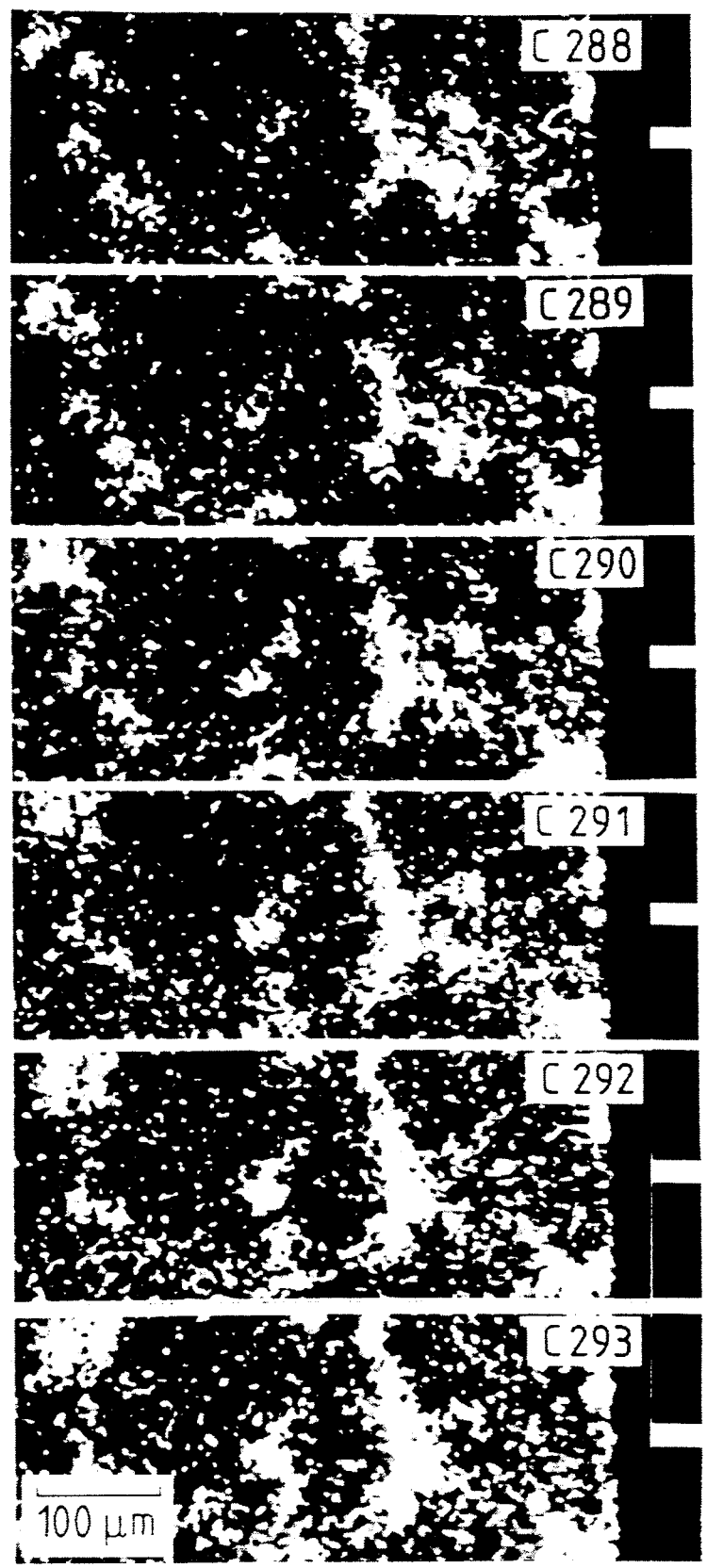
FIG. 16 is a micrograph of a set of six cuts of the sample described in FIG. 11. Cuts C288 to C293 (FIG. 10) are shown. The white bars on the right denote the location of the set of neighboring slices shown in FIG. 15.

In order to illustrate the structure of phases in three dimensions further, we show in FIG. 15 a set of six neighboring slices (S79 to S84) and in FIG. 16 a set of six neighboring cuts (C288 to C293) of sample 1. The distance between the mid planes of the neighboring slices (cuts) is about 2.8 $\mu$m. This value is the resolution as defined in section 2. For sample 1 it is given by the CCD pixel size (6.8 $\mu$m) divided by the light optical magnification used (2.4). As is seen, the network structures change continuously when passing through the stack of neighboring XTM micrographs. Taking FIGS. 11, 12, 15, and 16 together, it becomes evident that the structures seen are a network consisting of intermetallic phases which extend in three dimensions, and which have a mesh size on the order of 15 $\mu$m. We believe this is the first time such fine and interconnected structures have been visualized nondestructively and in 3-D.

Figure 18B:
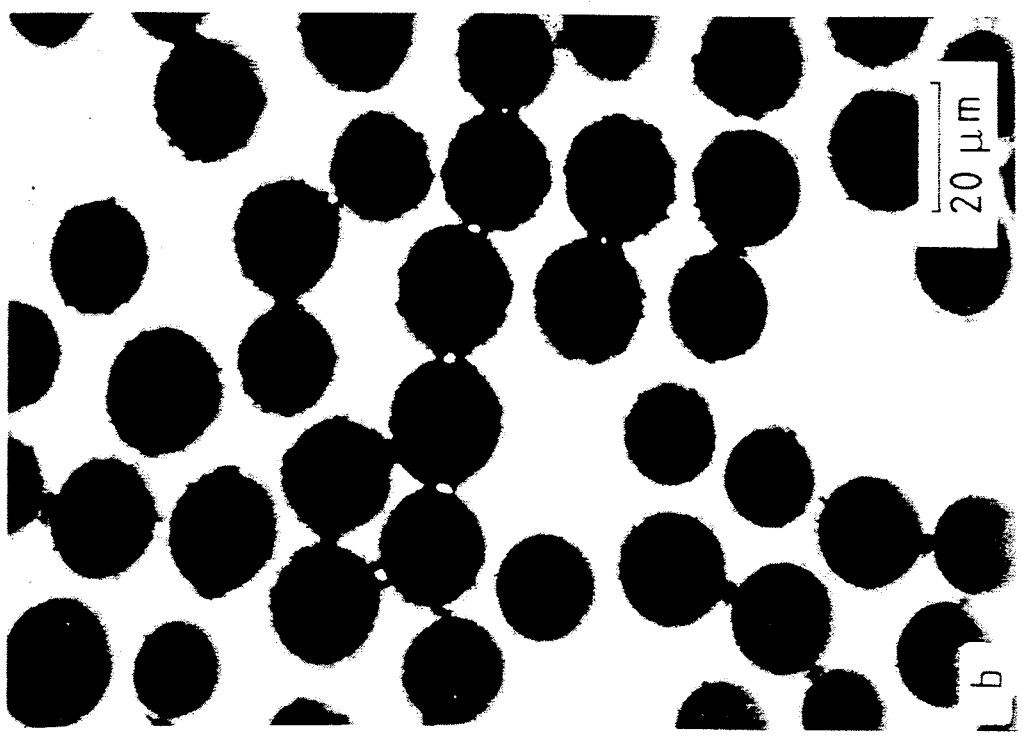
FIG. 18(a,b) s an XTM micrograph of another sample with orientation normal to the rotation axes. b: BSE-map of the sample.
Figure 18A:
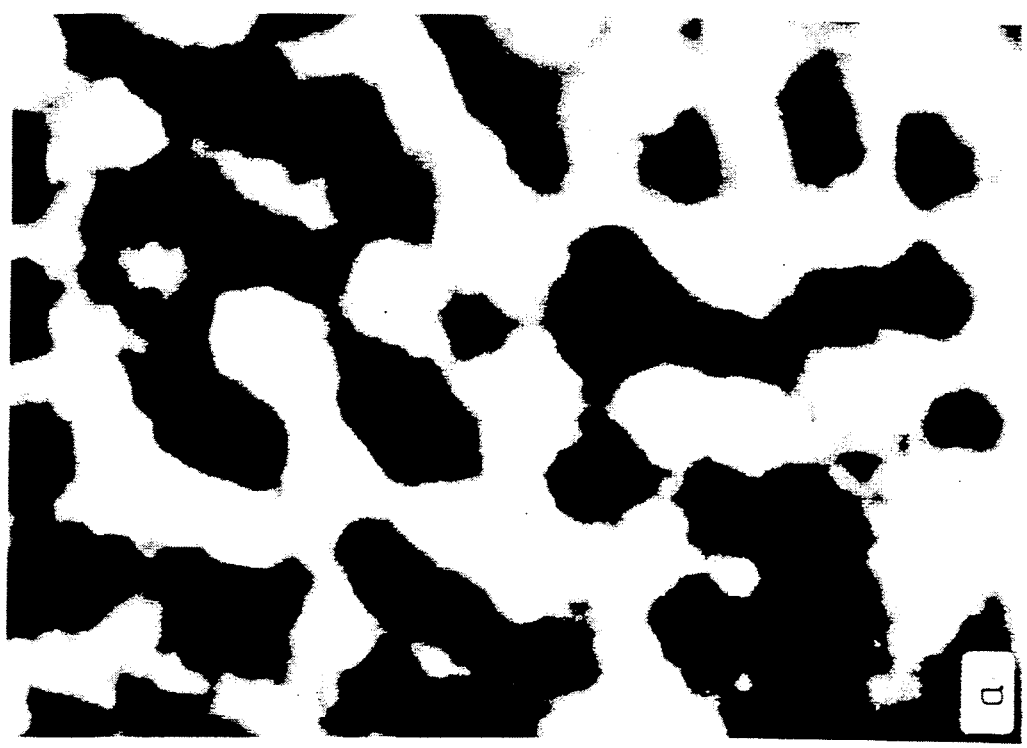

FIG. 18a is a XTM micrograph of sample 2 taken normal to its rotation axis by employing the Thomson CSF TH7882CDA CCD combined with a x-ray optical magnification of 5.8 and a light optical magnification of 2.04. Since, in sample 2, all fibers are oriented normal to the image plane, we interpret the dark dots as cuts through individual fibers. The fiber diameter of 15-20 $\mu$m as well as the distribution of fibers is in agreement with the scanning electron micrograph FIG. 18b and also FIG. 19, which shows a single fiber at even higher spatial resolution.

The resolution of the XTM picture, FIG. 18a, when calculated simply from the CCD pixel size (23 $\mu$m) and the overall magnification (11.8x), should be 23/11.8 ~2 $\mu$m. The modulation transfer function (MTF) measured for this imaging system, U. Bonse et al, HASYLAB Jahresbericht (DESY, Hamburg, 1988), p.557, yields 80 line pairs/mm at 20% contrast, corresponding to about 6 $\mu$m resolution. This is not far from what one would estimate just by looking at FIG. 18a.

Furthermore, we should point out that the MTF accounts for the resolution with respect to directions parallel to the reconstructed slices, i.e., normal to the axis about which the sample is rotated (FIGS. 8 and 10) when the projections are measured. At right angles to this plane, i.e., parallel to the rotation axis, there is no x-ray optical magnification, which means that the resolution in this direction is expected to be poorer by a factor of 5.8. Hence the image is integrated normal to the image plane over a depth of roughly 12 $\mu$m which accounts for an additional loss of resolution. It could be avoided by placing behind 68 in FIG. 8 a second crystal magnifier, diffracting at right angle with respect to the first one. With the second magnifier in the beam we estimate the intensity to drop by an order of magnitude.

A single magnifying crystal, diffracting in a plane perpendicular to the axis of sample rotation, although directly enlarging each projection only in one dimension, causes the reconstructed image to become magnified in two dimensions. When the projections are measured, a very large number of one-dimensional magnifications of sample projections in different directions are made. The reconstruction algorithm transforms the multi-directional one-dimensional magnifications of projections into the two-dimensionally magnified final image Hence, a kind of 'balance' between the amount of measured information and the amount of information contained in the reconstructed image is maintained. On the other hand, a crystal magnifier which is diffracting in a plane parallel to the sample's rotation axis, yields only a one-dimensional magnification of the reconstructed image.

The observations also confirm our theoretical estimates of resolution for the case when x-ray optical magnification is employed. Moreover, from the foregoing, we obtain substantial support for our thesis that by combining the techniques of magnification with the high resolution CCD and using a wiggler SR source, it will be possible to really achieve 3-D resolution on the scale of 1 micron and better for the XTM system.

A major advantage of the system of the invention over the pinhole or photodiode techniques is that all of the data for three-dimensional imaging can be acquired in parallel. Data-acquisition times have been reduced to a few hours. Also, the cooled CCD has a tremendous dynamic range ($10^3$) and is not as subject to nonlinearities as photodiode arrays are. The system of the invention has a three-dimensional resolution of better than 10μm. In addition, when elemental or phase-mapping details are desired, excellent chemical contrast can be obtained by recording data at two x-ray wavelengths (usually above and below a characteristic absorption edge) and performing image subtraction to enhance chemical or phase-specific information. Conventional CT technology typically uses a polychromatic beam from conventional tube sources, which effectively precludes quantitative chemical analysis.

The foregoing description of preferred embodiments of the invention has been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application, to thereby enable others skilled in the art to best utilize the invention in various embodiments and with various modifications, as are suited to the particular use contemplated. It is intended that the scope of the invention be defined by the claims appended hereto.

I claim:

1. A computerized three-dimensional x-ray tomographic microscopy system comprising in combination a source of parallel x-rays, and sequentially positioned in the path of said x-rays, a monochromator, a collimator, a sample stage, a two-stage asymmetric channel cut x-ray image magnifier, a scintillator, a lens, a charge coupled device, a controller electronically connected to said charge coupled device, an integrating computer electronically connected to said controller, and means for rotating said sample stage in stepwise manner controlled by said computer.

2. The tomographic system of claim 1 wherein said two-stage channel cut x-ray image magnifier is an asymmetrically cut Si (220) - Si (220) combination of crystals in a double crystal configuration.

3. In a computerized three-dimensional x-ray tomographic system containing a source of parallel x-rays, a sample stage, a detector system and an analyzing computer, the improvement of said detector system containing a two-stage asymmetric channel cut x-ray image magnifier.

4. The tomographic system of claim 3 wherein said asymmetric channel cut x-ray image magnifier is a asymmetrically cut Si (511) - Si (333) combination of crystals in a double-crystal configuration, wherein the diffracting plane of one of said crystals is positioned 90° with respect to the other.

5. A computerized three-dimensional x-ray tomographic microscopy system comprising a source of parallel x-rays, and sequentially positioned in the path of said rays a sample stage, a detector system and an analyzing computer, wherein said detector system contains at least one two-stage asymmetric channel cut x-ray image magnifier.

6. The system of claim 5 wherein said magnifier comprises an Si (511) - Si (333) combination of crystals in a double crystal configuration.

7. A process for magnifying x-ray images which comprises:
   (a) providing a beam of parallel x-ray beams,
   (b) passing said beams through a sample to be analyzed,
   (c) magnifying said beams, by passing them through with a two-stage asymmetric channel cut x-ray image magnifier,
   (d) converting said magnified beams to visable
   (e) recording the intensity of said visible light,
   (f) storing the recorded information obtained in a computer,
   (g) rotating the sample a pre-determined distance,
   (h) repeating steps (a) through (f),
   (i) repeating steps (g) and (h) a sufficient number of times to rotate the sample through 180o, and
   (j) converting the two-dimensional data recorded and stored into a three dimensional representation.

8. The process of claim 7 wherein said two-stage asymmetric channel cut x-ray image magnifier comprises an Si(511) - Si(333) combination of crystals in a double crystal configuration.

9. The process of claim 7 wherein said x-ray beam is converted to visable light by a scintillator.

10. The process of claim 7 wherein the intensity of said visible light is recorded with a charge coupled device.

11. The process of claim 7 wherein said two dimensional data is converted into three dimensional representations with software.

12.

13. The crystal of claim 12 which comprises an Si(511) - Si(333) combination of crystals in a double crystal configuration, wherein the diffracting plane of one of said crystals is positioned 90° with respect to the other.

14. An x-ray image magnifier which comprises two asymmetric channel cut monolithic crystals, one of said crystals being ninety degrees rotated with respect to the other, each of said crystals comprising a base having a substantially smooth upper surface, a first plate projecting vertically from said upper surface of said base having a smooth inwardly facing face, a second plate projecting vertically from said upper surface of said base having a smooth inwardly facing plate, at least one of said plates being adjustable with respect to the other, said faces of said first and second plates being asymmetrical with respect to each other.

15. The magnifier of claim 14 wherein said crystals comprise an Si(511) - Si(333) combination of crystals.

16. In a computerized three-dimensional x-ray tomographic microscopy system comprising in combination a source of parallel x-rays, and sequentially positioned in the path of said x-rays, a first monochromator, a collimator, a sample stage upon which is mounted a sample, a second monochromator, a scintillator, a lens, a charge coupled device, a controller electronically connected to said charge coupled device, an integrating computer electronically connected to said controller, and means for rotating said sample in stepwise manner controlled by said computer, the improvement of: said second monochromator being replaced by a two-stage asymmetric channel cut x-ray image magnifier.

17. The tomographic microscopy system of claim 16 wherein said x-ray image magnifier is asymmetrically cut Si (511) - Si (333) combination of crystals in a double crystal configuration.

18. In a computerized three-dimensional x-ray tomographic microscopy system comprising a source of parallel x-rays, a sample stage upon which is mounted a sample, a detector system and an analyzing computer, the improvement of said detector system containing a two-stage asymmetric channel cut x-ray image magnifier.

19. The tomographic system of claim 18 wherein said asymmetric channel cut x-ray image magnifier is a asymmetrically cut Si (511) - Si (333) combination of crystals in a double-crystal configuration.

20. An x-ray magnification system which comprises:
 a) source means for providing a parallel x-ray beams,
 b) staging means for staging and sequentially rotating a sample to be positioned in the path of the beam,
 c) x-ray image magnifier means positioned in the path of the beam downstream from the sample,
 d) detecting means for detecting the beams after being passed through and magnified by the image magnifier means, and
 e) computing means for analyzing values received from the detecting means, and converting the values into three-dimensional representations.

21. A process of x-ray tomographic image magnification which comprises:
 a) providing a parallel x-ray beam,
 b) passing the beam through a sample as it is being rotated in a predetermined sequence,
 c) magnifying the beam after it has passed through the sample,
 d) detecting the beam after it has been magnified, and converting it into electronic values, and
 e) analyzing the electronic values and converting the values into three-dimensional representations.

* * * * *